United States Patent
Harman et al.

(10) Patent No.: US 11,292,640 B2
(45) Date of Patent: *Apr. 5, 2022

(54) PREPARATION OF THERAPEUTIC FOAM

(71) Applicant: BTG INTERNATIONAL LIMITED, London (GB)

(72) Inventors: Anthony David Harman, London (GB); Jan Willem Marinus Mijers, Haarlem (NL); Nikki Robinson, London (GB)

(73) Assignee: BTG International Limited

( * ) Notice: Subject to any disclaimer, the term of this patent is extended or adjusted under 35 U.S.C. 154(b) by 16 days.

This patent is subject to a terminal disclaimer.

(21) Appl. No.: 17/021,739

(22) Filed: Sep. 15, 2020

(65) Prior Publication Data

US 2021/0002039 A1 Jan. 7, 2021

Related U.S. Application Data

(63) Continuation of application No. 14/470,102, filed on Aug. 27, 2014, now Pat. No. 10,773,864, which is a continuation of application No. 12/801,645, filed on Jun. 18, 2010, now abandoned, which is a continuation of application No. 11/919,749, filed as application No. PCT/GB2006/001744 on May 12, 2006, now abandoned.

(30) Foreign Application Priority Data

May 13, 2005 (GB) ...................................... 0509845

(51) Int. Cl.
| | |
|---|---|
| B65D 51/00 | (2006.01) |
| A61J 1/20 | (2006.01) |
| A61K 9/12 | (2006.01) |
| A61K 31/08 | (2006.01) |
| B65D 47/06 | (2006.01) |
| A61J 1/14 | (2006.01) |
| B65D 83/14 | (2006.01) |

(52) U.S. Cl.
CPC ............ *B65D 47/06* (2013.01); *A61J 1/1406* (2013.01); *A61J 1/1437* (2013.01); *A61J 1/2096* (2013.01); *A61K 9/122* (2013.01); *A61K 31/08* (2013.01); *B65D 51/002* (2013.01); *B65D 83/756* (2013.01); *A61J 1/201* (2015.05); *A61J 1/2037* (2015.05); *A61J 1/2086* (2015.05)

(58) Field of Classification Search
None
See application file for complete search history.

(56) References Cited

U.S. PATENT DOCUMENTS

| | | | |
|---|---|---|---|
| 3,578,037 A | 5/1971 | Flynn | |
| 3,685,514 A | 8/1972 | Cheney | |
| 4,557,722 A | 12/1985 | Harris | |
| 5,775,671 A | 7/1998 | Cote | |
| 5,921,419 A | 7/1999 | Niedospial, Jr. et al. | |
| 6,050,978 A | 4/2000 | Orr et al. | |
| 6,073,759 A | 6/2000 | Lamborne et al. | |
| 6,572,873 B1 | 6/2003 | Osman et al. | |
| 6,942,165 B1 | 9/2005 | Osman et al. | |
| 7,025,290 B2 | 4/2006 | Osman et al. | |
| 7,814,943 B2 | 10/2010 | Harman et al. | |
| 7,842,282 B2 | 11/2010 | Harman et al. | |
| 7,842,283 B2 | 11/2010 | Harman et al. | |
| 10,472,100 B2 | 11/2019 | Wright et al. | |
| 10,773,864 B2 * | 9/2020 | Harman | B65D 51/002 |
| 2002/0077589 A1 | 6/2002 | Tessari | |
| 2003/0082243 A1 | 5/2003 | Harman et al. | |
| 2005/0148903 A1 | 7/2005 | Diamantopoulos | |
| 2006/0074386 A1 | 4/2006 | Wollmann | |
| 2009/0124961 A1 | 5/2009 | Harman | |
| 2013/0189192 A1 | 7/2013 | Harman | |
| 2014/0343484 A1 | 11/2014 | Wright et al. | |
| 2017/0157046 A1 | 6/2017 | Osman et al. | |

FOREIGN PATENT DOCUMENTS

| | | |
|---|---|---|
| EP | 1331031 A2 | 7/2003 |
| FR | 2775433 A1 | 9/1999 |
| WO | 0147571 A2 | 7/2001 |
| WO | 2004041656 A2 | 5/2004 |
| WO | 2004047969 A1 | 6/2004 |
| WO | 2005048976 A2 | 6/2005 |
| WO | 2005105014 A2 | 11/2005 |

* cited by examiner

*Primary Examiner* — Katherine Peebles

(74) *Attorney, Agent, or Firm* — Seager, Tufte & Wickhem, LLP

(57) ABSTRACT

A device is described for facilitating the preparation of therapeutic foam e.g. for the treatment of varicose veins. A pressurised vial contains a sclerosant liquid, e.g., polidocanol solution, and a sterile gas which is readily absorbed by the body, e.g., carbon dioxide, oxygen or a mixture of these gases. The vial is provided either with a specialised stopper/seal into which a syringe nozzle may be inserted or alternatively a septum seal which may be penetrated by a hypodermic needle. The quantities of gas and liquid and the pressure in the vial are pre-set so that, on connection of a syringe to the vial, a predetermined volume of both gas and liquid is transferred to the syringe, with the intention that the syringe is then used to make a foam by known means. The use of the vial ensures that the ratio of gas to liquid in the foam is standardised, and also provides a convenient way of packaging the gas and liquid and of filling the syringe in a sterile manner.

10 Claims, 3 Drawing Sheets

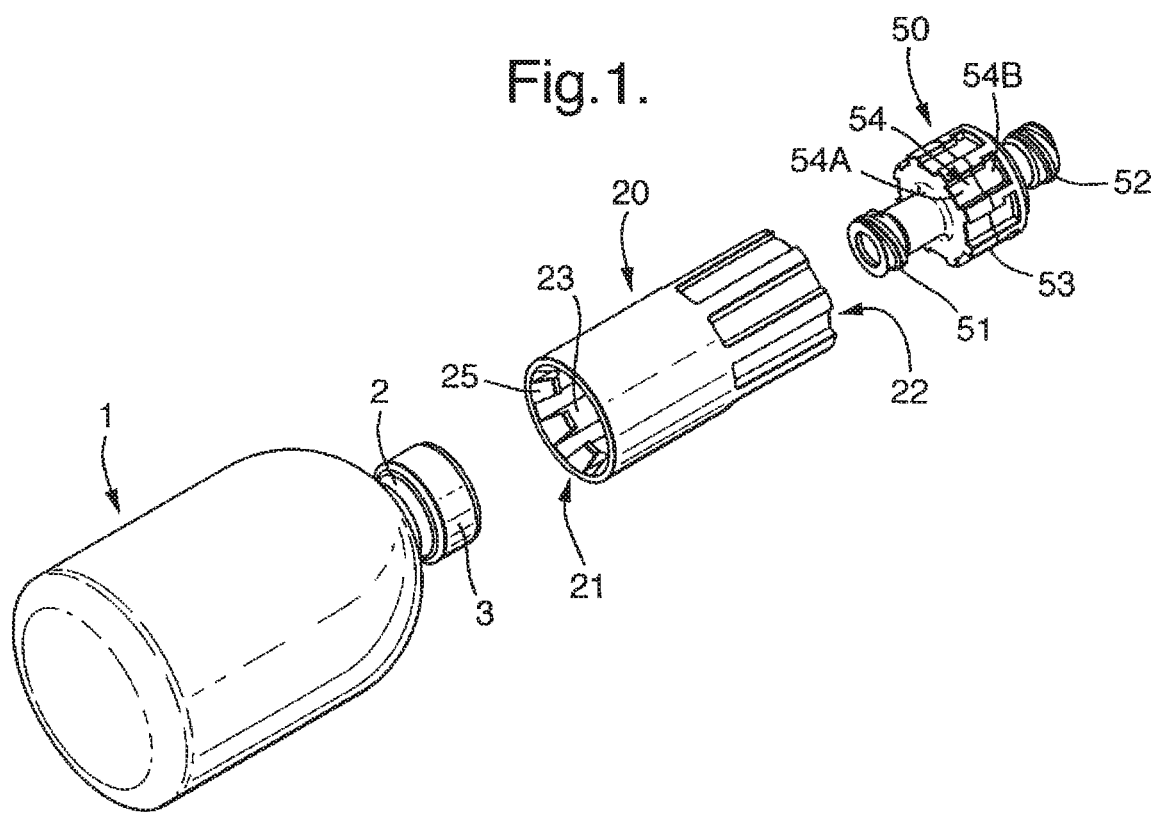
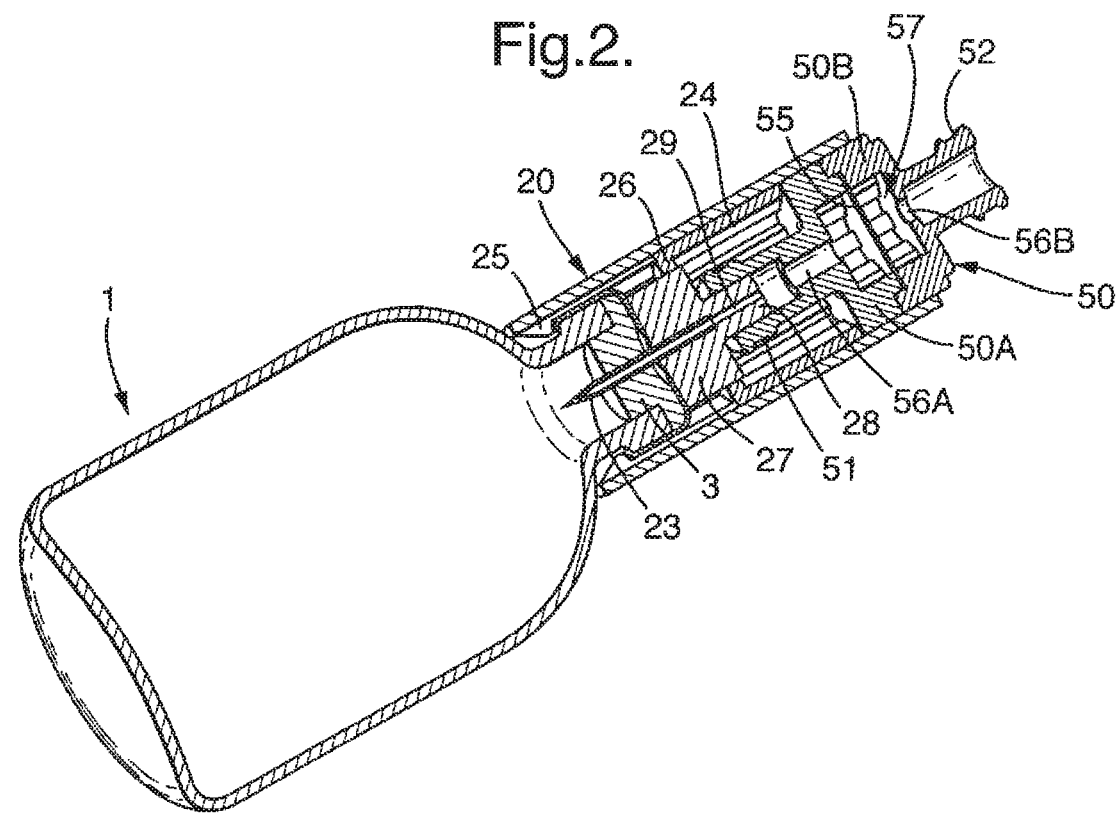

PREPARATION OF THERAPEUTIC FOAM

CROSS-REFERENCE TO RELATED APPLICATIONS

This application is a continuation of U.S. patent application Ser. No. 14/470,102, filed Aug. 27, 2014, now U.S. Pat. No. 10,773,864, which is a continuation of U.S. patent application Ser. No. 12/801,645, filed Jun. 18, 2010, abandoned, which is a continuation of U.S. patent application Ser. No. 11/919,749, filed Jan. 25, 2008, abandoned, which is a national stage filing under 35 U.S.C. § 371 of International Application No. PCT/GB2006/0017744, filed on May 12, 2006, which claims the benefit of priority to British Patent Application No. 0509845.4, filed May 13, 2005, the entire contents of each of which are hereby incorporated by reference.

BACKGROUND OF THE INVENTION

The present invention relates to apparatus and a method for dispensing predetermined quantities of liquid and gas into a syringe or similar device and also to a pack containing a syringe or other vessel charged with liquid and gas. The invention relates especially to syringes or other vessels charged with predetermined quantities of a foamable clinical grade liquid, e.g. a sclerosant liquid for treatment of varicose veins, and a gas other than air.

Foam preparations of sclerosant chemicals can be very useful in the treatment of varicose veins and other malformed vessels in the body. The injection of foam into varicose veins has many advantages over the injection of sclerosant liquid; a foamed product allows a large area of internal vessel wall to be exposed to the active, for a given total quantity of the active in the vein. Foam with the right characteristics is able to displace blood from the vein, preventing dilution of the drug, as happens with liquid.

SUMMARY OF THE INVENTION

It is likely that many other medical applications for clinical foam preparations will be developed in the future, including but not limited to the sclerosing of the internal surfaces of other vessels and cavities in the body.

A problem with foamed clinical preparations is the production of a consistent, sterile product for use by a physician. A further issue is the potential danger of injecting quantities of air into the body, since nitrogen is highly insoluble. Extemporaneously prepared foams made with air are widely used, but work conducted by the inventors has shown that even the smallest volumes of nitrogen, of the order of a few percent, give rise to bubbles which endure in the vascular system and are potentially harmful. These issues are discussed at length in co-pending applications numbers PCT/GB04/004824, PCT/GB04/004831, PCT/GB04/004846 and PCT/GB04/004848, the contents of which are incorporated herein by reference.

Many of the current extemporaneous methods of foam production rely on drawing a small quantity of liquid into a syringe, together with a large quantity of air, and then agitating the mixture by some means to produce a foam. It is possible using these techniques to produce a good quality homogeneous foam with microscopic bubbles ("microfoam"), but it is equally possible to produce a poor quality foam: the properties of the foam are dependent on a number of factors including the amount of energy put into making the foam, and the ratio of gas to liquid in the syringe.

It is preferable to prepare the foam with gasses such as oxygen or carbon dioxide, which will be absorbed by the body much more readily; this is discussed in other patents and patent applications in the name of the applicants details of which are given above. However, there are difficulties for a physician wishing to fill a syringe exclusively with a gas other than air. The most straightforward method would be to connect the nozzle of the syringe to a line from a cylinder of the desired gas, but it is difficult reliably to exclude all air/nitrogen and virtually impossible to check the purity of the gas component in the syringe. Alternatively, one could fill a fume cupboard or similar with an appropriate gas or gas mixture and fill the syringe in the fume cupboard. However, this involves a large amount of gas being provided to fill the fume cupboard when only a very small amount of gas is necessary to fill the syringe. Furthermore, it is still difficult to be confident that the contents of the fume cupboard, and therefore the gas in the filled syringe, are exclusively the desired gas or gas mix.

The applicants are currently developing a pressurised canister product for generating a sclerosant foam from a polidocanol solution and a gas mixture comprising oxygen and carbon dioxide or comprising substantially pure oxygen. Considerable effort has gone into ensuring that the foam product is optimised in every way for the varicose vein sclerotherapy application for which it is intended, that the foam is sterile and that a foam of the required properties is consistently produced. The canister product is designed to be very simple to operate so that a physician can concentrate on treating the patient rather than on setting up apparatus to produce foam and ensuring the foam is of adequate quality.

It is recognised by the applicants that the canister product, whilst having all the advantages described above, is relatively expensive. Syringe-based systems for generating foam are less expensive and capable of producing good quality foam, provided that some essential parameters are determined sufficiently accurately, reliably and consistently and provided that sterility can be ensured. Of these parameters, the most important is ensuring that the starting mix is correct, that is to say that the volume of liquid and volume of gas are correct and that the composition of the gas is correct.

An alternative known technique comprises connecting a syringe to a vial containing foamable liquid and air in the correct proportions, but with the plunger of the syringe drawn back. The plunger of the syringe is then pumped in order repeatedly to pressurise the contents of the vial. This can result in an acceptable foam being generated in the vial and/or syringe. This method has the advantage of providing predetermined volumes of gas and liquid. The problem of incorporating a gas other than air remains, however; in order for this technique to produce acceptable foam, the vessel must be repeatedly pressurised, so simply replacing the air in the vessel with another gas will not work since the syringe would need also to be filled with the same gas The present invention provides apparatus which may be suitable for use with both the syringe based technique and the vial based technique described above.

According to a first aspect of the present invention a vessel is provided having sterile contents comprising in predetermined proportions (i) a foamable liquid and (ii) a gas or gas mixture other than air, the contents being at a pressure substantially above atmospheric, the vessel having an outlet adapted to cooperate with a syringe nozzle, the said outlet having associated with it a seal or valve adapted to be broken or opened respectively by the action of inserting a syringe nozzle into the outlet, with additional force to break or open the seal or valve. Alternatively, the seal or valve may be broken or opened by the user after the nozzle has been inserted.

The pressure of the vessel contents is preferably 1.3 bar absolute ("bara") or more (i.e. 1.3 times atmospheric pressure), more preferably 1.5 bara or more, more preferably 1.8 bara or more, still more preferably 2 bara or more or possibly 2.5 bara or more. The pressure is preferably less than 10 bara, more preferably less than 5 bara and most preferably less than 3 bara.

The outlet preferably comprises a female luer connector. The pressurised gas preferably consists essentially of oxygen, carbon dioxide or a mixture thereof. It may include one or more of: helium, nitrous oxide, neon, argon, xenon or sulphur hexafluoride. The liquid is preferably a sclerosant liquid solution, e.g. polidocanol, preferably 1% polidocanol, sodium tetradecyl sulphate, ethanolamine oleate, sodium morrhuate, hypertonic glucosated or glucosaline solutions, chromated glycerol or iodated solutions. Other sclerosing solutions will be known to the person of average skill in the art.

In a preferred embodiment, the outlet may be formed in a fluid transfer assembly which may include a frangible or detachable valve assembly which may be removed with the syringe after filling. The valve assembly may function as a syringe stopper or alternatively a syringe connector for connecting a second syringe to the first. In the case that the valve assembly is designed to function as a syringe stopper, it need not necessarily be frangible/detachable as will be explained in more detail below.

Alternatively, in a second aspect of the invention a vessel is provided having substantially sterile contents comprising in predetermined proportions (i) a foamable liquid and (ii) a gas or gas mixture other than air, the contents being at a pressure substantially above atmospheric, the vessel having a resilient closure such as a rubber septum which is pierceable by a hypodermic needle or similar, and which forms a seal around the needle when it is pierced.

In the case of the present invention where the vessel is at above atmospheric pressure, the resilient closure preferably has substantial thickness e.g. of 1 mm or more, preferably 2 mm or more, but less than 30 mm, more preferably less than 10 mm. The reason for this is that most hypodermic and similar needles have a bevelled end which forms the point. It is possible, during insertion of such a needle through a thin septum, to create briefly a leakage path between the interior and exterior of the vessel through which gas may be exhausted from the vessel to atmosphere. This is undesirable because the pressure in the vessel would then be at an unknown level and an incorrect volume of gas may be dispensed into the syringe. Preferably, the septum is also under a degree of radial compression, to ensure that the seal around the needle point is made.

The needle would normally be inserted to the bottom of the vessel, whilst the syringe plunger is held in manually. The vessel would be held upright, i.e. with the septum uppermost, and the syringe plunger released. Gas pressure in the vessel would force the liquid up the needle, and then the pressure would equalise, in the process forcing the syringe plunger further back. Alternatively, the vessel could be held upside down and the needle inserted a relatively small, but predetermined, distance into the vessel. There would be a residual quantity of liquid remaining in the vessel after transfer of the contents to a syringe, and the volume of liquid in the vessel to start with would be calculated to take this into account.

In the second aspect of the invention a fluid transfer assembly may house a needle for piercing the resilient seal or septum of the vessel. The assembly may comprise formations for attaching the assembly to the top of the vessel such that the needle pierces the septum and enters the vessel to a predetermined depth. The fluid transfer assembly may also include a frangible or detachable valve assembly which may be removed with the syringe after filling. The fluid transfer assembly may function as a one way valve or alternatively a syringe connector for connecting a second syringe to the first. In the case that the fluid transfer assembly is designed to function as a one way valve, it need not necessarily be frangible/detachable as will be explained in more detail below.

As with the first aspect of the invention discussed above, the pressurised gas preferably consists essentially of oxygen, carbon dioxide or a mixture thereof. It may include one or more of: helium, nitrous oxide, neon, argon, xenon or sulphur hexafluoride. The liquid is preferably a sclerosant liquid solution, e.g. polidocanol, preferably 1% polidocanol, sodium tetradecyl sulphate, ethanolamine oleate, sodium morrhuate, hypertonic glucosated or glucosaline solutions, chromated glycerol or iodated solutions. Other sclerosing solutions will be known to the person of average skill in the art.

Also as with the first aspect of the invention, the pressure of the vessel contents is preferably 1.3 bar absolute ("bara") or more (i.e. 1.3 times atmospheric pressure), more preferably 1.5 bara or more, more preferably 1.8 bara or more, still more preferably 2 bara or more or possibly 2.5 bara or more. The pressure is preferably less than 10 bara, more preferably less than 5 bara and most preferably less than 3 bara.

The two principal methods for making foam using a syringe are as follows. In the first method, the syringe is provided with an additional plunger received telescopically within the main plunger of the syringe. This plunger is provided with one or more apertures—holes or slots—and, in use, is reciprocated within the syringe barrel to agitate the contents and create a foam. In the second method, a second substantially conventional syringe is attached to the first via a connector element which comprises two female luer connectors which communicate via one or more small apertures, e.g. an aperture of 0.5 mm or so, or alternatively a porous membrane or mesh having very small apertures measured in microns. The contents of the syringes are then passed back and forth to create a foam.

It will be appreciated that the valve assembly of the fluid transfer assembly may be designed such that, once removed with the syringe, it forms either a one way valve for a device of the first type or a connector for a device of the second type. If it is to form a one way valve for the first type of syringe device, then the valve assembly may alternatively remain part of the fluid transfer assembly during generation of the foam.

According to the invention, a system for filling a syringe with predetermined volumes of air and gas comprises a vessel and fluid transfer assembly according to any of the descriptions given above, together with a syringe. The syringe may comprise a syringe barrel, main syringe plunger and a secondary plunger capable of reciprocal motion within the barrel independent of the main plunger, the second plunger having a plunger head provided with apertures therein. Alternatively the system may comprise a vessel as described above together with two syringes.

A method according to the first aspect of the invention described above comprises inserting the nozzle of a syringe into the outlet of a vessel as described above so as to break a seal or open a valve, thereby causing the liquid in the vessel to flow under pressure into the syringe and the pressure of gas to equalise between the syringe and the vessel. Preferably, since the needle extends a relatively small distance into the vessel, the method includes the initial step of ensuring that the vessel is in an inverted position with its outlet pointing downwards; thereby the liquid in the vessel is transferred to the syringe under pressure before the gas pressure equalises.

An a modification, a dip tube could be provided in the vessel in which case the vessel would be kept in an upright orientation during transfer of its contents to a syringe.

Another definition of the method of the first aspect is the following sequence of steps:
- (a) Providing a syringe, together with a vessel containing a foamable liquid and a gas or gas mix other than air at a pressure substantially above atmospheric pressure, the contents of the vessel being substantially sterile;
- (b) Connecting the syringe to the vessel such that predetermined masses of liquid and gas are transferred to the syringe.

A method of creating a foam in a syringe may comprise the above steps (a) and (b) followed by the steps:
- (c) Removing the charged syringe from the vessel;
- (d) Attaching a second syringe in a closed state to the first
- (e) Pumping gas and liquid between the syringes to generate a foam.

Another aspect of the invention is presented below, which also addresses the problem of reliably providing a syringe filled with the correct proportions of liquid and a gas other than air.

According to this aspect, the syringe or other vessel is supplied prepackaged, charged with the correct gas and liquid in the correct amounts. Thus, according to the present invention a sterile pack is provided, containing a syringe charged with a sclerosant liquid solution and a gas, wherein the gas consists essentially of carbon dioxide, oxygen, helium, nitrous oxide, xenon, neon or sulphur hexafluoride, or a mixture of two or more of those, the ratio of liquid to gas being in the range 0.05 g/ml to 0.25 g/ml, preferably 0.07 g/ml to 0.2 g/ml, more preferably 0.1 g/ml to 0.16 g/ml.

The syringe may be made from glass or another material which is substantially impermeable to these gases. However, such materials can be expensive/fragile/dangerous/opaque. If the syringe is made from the type of plastics material which is standard for such applications, the shelf life of the product may be quite short since some or all of these gases tend to diffuse through such plastics.

It is preferable, especially if the syringe is to be made from the conventional type of plastics material, for the syringe and/or the pack to be designed in such a way that diffusion is substantially eliminated. This may be done by treating the surface of the syringe and/or plunger head or by making the plunger head of a material substantially impermeable to these gases. Treatment may involve metallising (normally using aluminium) the surface or coating it with some other material which is substantially impermeable to these gases. The coating—both in terms of material and thickness—may depend on which gases are used in the syringe: helium is a very small molecule which will diffuse through many materials whilst oxygen is much larger and therefore easier to contain for a period long enough to constitute a reasonable shelf life for this sort of product.

A potential problem with treating the surface of the syringe is that it may result in reduced, or even no, visibility for the user of the contents of the syringe. Another solution, and the preferable one, is to package the syringe in a pack made from material which is impermeable to the gas or gases being used. For example the syringe may be packaged in a bag made from metallised plastics material. This type of packaging, namely metallised plastics film, is widely used for other applications and is therefore readily available and is inexpensive.

Gas may still diffuse out of the syringe into the space surrounding it within the pack. Therefore it is preferred that the syringe be vacuum packed in the bag or, alternatively that the bag contains a gas atmosphere substantially the same as the gas or gas mixture in the syringe.

Optionally the syringe could be both treated/coated and packaged as described above as well as being packed in a vacuum or in an appropriate gas atmosphere.

As described above, there are two principal methods for making foam using a syringe: the first in which the syringe is provided with an additional plunger for foaming the liquid and gas mix, and the second in which a further syringe is attached and the gas and liquid pumped between the syringes.

According to the invention, a syringe of the first type may be provided, charged with appropriate amounts of liquid and physiological gas and packaged and/or treated as described above.

Also according to the invention, a conventional syringe may be provided, charged with appropriate amounts of liquid and physiological gas and packaged and/or treated as described above. A pack containing two such syringes could be provided, optionally also with a connector having a narrow bore or mesh. The two syringes and connector may be in a kit form or may be assembled with the luer nozzles of the syringes mounted together by means of the connector.

A difficulty arises in sterilising the products described above. If the syringe is made from conventional plastics, whether coated or not, it may be unsuitable for sterilisation by autoclaving. This leaves gamma sterilisation as the main alternative, but the liquid with which the syringe is charged may not compatible with gamma sterilisation techniques. This is the case if the liquid is polidocanol solution, which is the preferred chemical for sclerosis of varicose veins.

Two alternative solutions to this problem have been devised. The first is to provide polidocanol, or another active, in a lyophilised or freeze dried form which is compatible with gamma sterilisation. In this case, preferably the lyophilised active would be provided in one syringe and sterile solvent, e.g. water or saline, in another. The physiological gas or gas mixture may be provided in either syringe; clearly the syringe with the physiological gas is preferably packaged or treated/coated as described above, though both syringes and optionally a connector as described above may be incorporated into the same pack. This pack may then be subjected to a gamma sterilisation process. In use, the two syringes are connected together and the contents passed rapidly between them. During this process the lyophilised active is reconstituted in the sterile water or saline and then a foam formed with the physiological gas.

The second solution is to manufacture the syringe pack using known aseptic techniques.

To avoid contamination, the pack contents may be at slightly above atmospheric pressure. This may be achieved by manufacturing the pack at an ambient temperature below standard room temperature. Once the pack enters normal ambient surroundings, the temperature increase of the atmosphere inside the pack will ensure a slight overpressure.

Very recently, a machine has been made available which is designed to receive two syringes and apply a given number of pumps at a given rate to achieve a roughly consistent product. The machine is called "Turbofoam"® but the inventors are not at present aware who is marketing the machine. Two syringes loaded into the machine (one of which is loaded with sclerosant solution and the other of which contains air). When activated, the machine automatically cycles the syringes until a foam of the desired properties is made. Clearly, this arrangement addresses at least the issues of reproducibility of the foam as regards the number and speed of cycles. However, it does not address sterility or the loading of the syringes with the correct quantities of gas and liquid.

A pre-packed syringe or other vessel, as described above, could constitute a cartridge for a foam generating machine similar to the "Turbofoam"® machine. This would solve the problems described above which the machine at the moment does not address (as well as of course providing for a more appropriate gas composition for the foam). Thus, according to another aspect of the invention, a cartridge for a machine for generating a clinical foam is provided, comprising a sterile pack enclosing a syringe or other vessel charged with a liquid active and a gas other than air. The preferable features described earlier also apply to this aspect.

Further features and advantages will become apparent from the following description of five embodiments of the invention, which is made with reference to the accompanying drawings, in which:—

BRIEF DESCRIPTION OF THE DRAWINGS

FIG. 1 is a perspective view of a first embodiment of the invention with separated components;

FIG. 2 is a perspective sectional view of the apparatus of FIG. 1 with the components assembled;

DETAILED DESCRIPTION OF PREFERRED EMBODIMENTS

Figure 3:
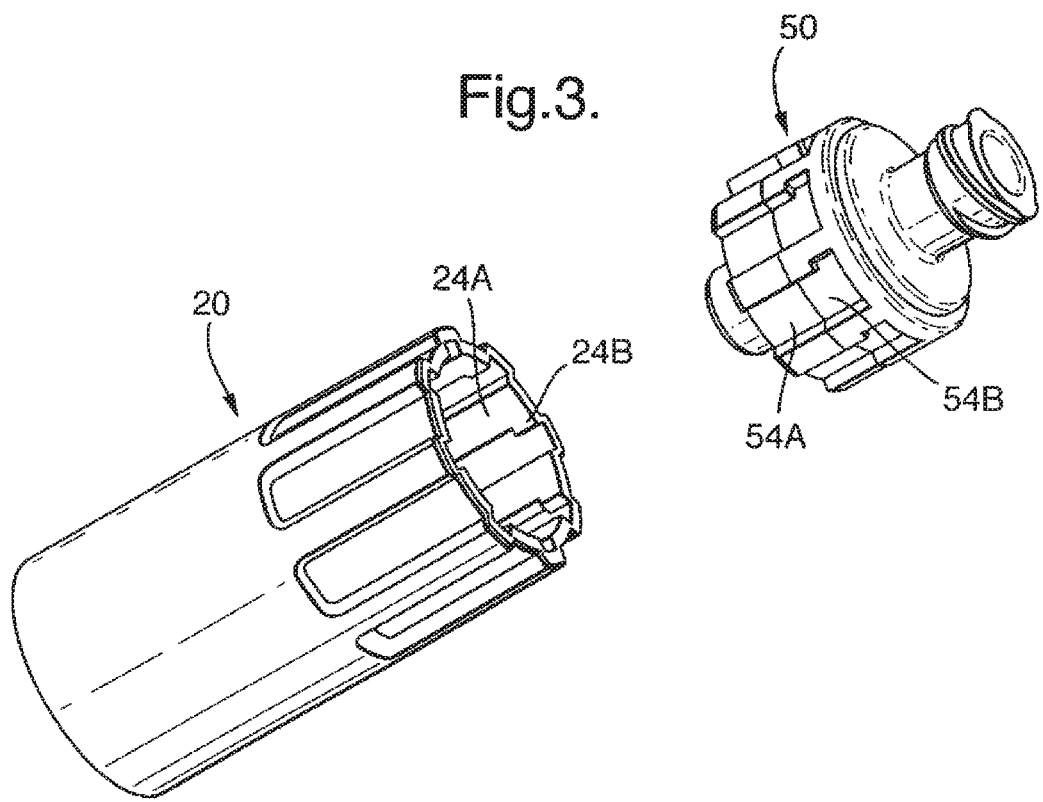
FIG. 3 is a perspective view from a different angle of two components of the apparatus of FIG. 1.

Referring to FIG. 1, a system for dispensing a liquid sclerosant and carbon dioxide gas into a syringe in predetermined quantities is shown. A vial 1 contains a measured volume of a 1% solution of polidocanol (a common sclerosant used in the treatment of varicose veins), in an atmosphere of pressurised carbon dioxide at a purity level of 99.5%.

The vial 1 has a neck region 2 to which is fitted with a resilient septum-type seal 3 of chlorobutyl or bromobutyl rubber material, under radial compression.

A fluid transfer device 20 of overall cylindrical shape has opposed first and second open ends 21, 22, the first end 21 being designed to fit over the neck 2 and seal 3 of the vial 1. Housed within the transfer device 20 is a hollow needle 23 adapted to puncture the seal 3 when the device is fitted to the vial 1. The tip of the needle 23 is recessed within the transfer device, set back from the first open end 21.

A syringe connector device 50 is adapted to fit into the second open end 22 of the transfer device 20. The connector device 50 comprises first and second female luer lock connections 51, 52 on respective sides of a central housing 53 which is provided with locking formations 54 designed to interface with corresponding locking formations on the interior wall of the transfer device 20. The locking formations on the connector 50 comprise L shaped grooves with a longer leg 54A oriented axially and a shorter transverse leg 54B. The complementary locking formations 24 on the interior wall of the transfer device 20 can be seen partly in FIG. 2 and partly in FIG. 3. These formations comprise L shaped lands having a longer leg 24A and a shorter leg 24B. The formations 24, 54 are designed such that the connector device 50 may be slid into place in the transfer device 20 and then rotated slightly about the overall axis of the system so that the shorter legs 24B, 54B of the locking formations interengage to lock the connector device 50 in place. A similar action in the opposite sense will unlock the connector device 50 and allow it to be removed from the transfer device 20. Both devices are moulded from a plastics material which will exhibit a degree of resilience, and the formations are dimensioned to allow for a slight interference as the short legs of the Ls engage. In practice, it is intended that the connector 50 and transfer device 20 would be supplied to the user ready-assembled.

Referring now to FIG. 2, the device can be seen in its assembled state with the needle 23 passing through the septum seal 3 of the vial 1. The septum 3 of the vial is relatively thick, of the order of 5 mm; the reason for this will be explained later.

The internal structure of the transfer device 20 and the connector 50 can be seen in FIG. 2. The transfer device is provided with attachment formations 25 on its interior surface, around the perimeter of the first open end. These formations 25 are barb-shaped in cross section and are arranged to snap over the mouth of the vial 1 and engage with the neck region 2 to attach the transfer device to the vial.

At approximately the middle of the transfer device is an internal transverse web 26 which supports a needle housing 27 in which the needle 23 is received. On the opposite side of the needle housing is a male luer connector formation 28, whose internal bore 29 is in communication with the bore of the hollow needle 23. In the assembled state, as shown in FIG. 2, the first female luer lock formation 51 of the connector device engages with the male luer formation 28 of the transfer device.

The connector device 50, as can be seen best in FIG. 2, is manufactured as two moulded plastics halves 50A, 50B which are ultrasound welded together. Each half 50A,B is formed with a bore 56A,B respectively communicating with the respective luer lock formation 51,52 on each moulding. Each moulding is formed with a recess on its side opposite its luer connector, such that when the halves 50A,B are secured together a cavity 57 is formed. Secured in place between the two mouldings 50A,B is a nylon mesh 55 which divides the cavity such that the only means of communication between the luer connectors 51,52 is via the pores of the mesh 55. The mesh has small pores of 5 micron maximum dimension. In a modification, a number of meshes, e.g. 3 or 4, could be used to improve foam homogeneity and/or reduce the number of strokes needed.

In use, as discussed above, these units would be supplied with the fluid transfer device 20 and the syringe connector device 50 already assembled and locked into place. The vial 1 would be supplied separate, though normally as part of a kit with the connector & transfer devices and with a pair of 20 ml syringes. The syringes are not illustrated in connection with this embodiment, but are standard plastics material 20 ml syringes equipped with luer lock nozzles.

The user first takes a 20 ml syringe and fits the luer nozzle to the exposed female luer lock formation 52 of the connector device 50, ensuring first that the plunger of the syringe is fully depressed. The vial 1 is then held with its neck and septum pointing downwards and the needle end of the transfer device 20 pushed over the neck 2 of the vial so that the barbed attachment formations 25 engage the vial 1 and retain the transfer and connector devices in place whilst the needle 23 pierces the septum 3 so that its open tip protrudes just beyond the interior surface of the septum 3.

As previously discussed, the vial contents are pressurised. On inverting the vial, the liquid contents (1% polidocanol solution) will occupy a region adjacent the septum whilst the remaining space inside the vial will be occupied by pressurised carbon dioxide. As soon as the needle punctures the septum, the polidocanol solution will be forced under pressure through the needle, then through the male luer connector 28 of the needle housing 27, female luer 51 of the connector 50, mesh 55, and then out of the connector 50 and into the syringe (not shown). Once all the liquid has been transferred (a small volume may remain at a lower level than the aperture in the tip of the needle 23), the pressure of the carbon dioxide in the vial will force carbon dioxide gas into the syringe until the pressures in the vial and syringe are substantially equalised. It is possible, because of the resistance offered by the plunger of the syringe, that the user will need to manually ease the plunger back to a predetermined point on the syringe scale; however, the vial is charged with carbon dioxide at a pressure designed to equalise when precisely the desired volumes of liquid and gas have been transferred to the syringe, so at most only a minimal amount of intervention by the user is required in this respect. The volume of liquid with which the vial is charged will take into account the residual volume of liquid which will remain in the vial "below" the open needle tip after transfer of fluid to the syringe.

The user should of course double check that the amount of liquid and gas, measured against the scale on the syringe, appears to be correct, before proceeding further.

The next step in the procedure is to detach the connector device and syringe. The user twists the assembled connector device and syringe, taking care not to release the luer connection between the two, so that the locking formations 24, 54 on the transfer device and connector device disengage. The user then removes the connector device, exposing the luer lock connector on the other side. The user then fits a further 20 ml luer lock syringe to the connector device 50, ensuring that the plunger of the second syringe is fully depressed before it is connected. The two syringes are then oscillated such that the gas and liquid pass a number of times back and forth through the connector device 50 and through the mesh 55 in the connector device. This step may be done manually or, preferably, is done by inserting the syringe pair into a simple desktop device such the "Turbofoam"® device described above which will automatically oscillate the syringes at a predetermined speed and for a predetermined number of cycles.

The first embodiment uses a modified version of what is popularly known as the "Tessari" method for generating foam, namely connecting two syringes containing air and sclerosant and passing the contents back and forth vigorously until a foam of appropriate characteristics is made. The first embodiment differs from this of course in that it involves a pressurised vial of sclerosant and gas as the source for the foam constituents. When a highly soluble gas such as carbon dioxide is used (because of its superior safety profile compared to air) this can make the foam more difficult to create since the solubility of the gas tends to break the foam down. For this reason a fine mesh is used rather than a simple connector between the syringes, and this mesh is conveniently incorporated into the connector device 50.

However, the mesh is not essential, and in a modification of the first embodiment, the mesh is omitted. In every other respect the system remains the same. More vigorous cycling of the gas and liquid is required to make the foam, and the foam may not endure as long as a foam made using the mesh. In a second modification of the first embodiment, baffles or one or more flow restrictions are provided in the connector device, in order to make the gas and liquid flow past edges in order to reduce the average bubble size. Providing projections at right angles to the flow direction will achieve this. Alternatively, the gas and liquid could be forced through one or more small passages (e.g. of the order of 0.1 to 1.0 mm diameter or maximum dimension). The exact structure is not critical. This modification has the advantage of making the passage of foam and gas through the connector device a lot easier than when a mesh is used, due to the larger open area, whilst also providing more disruption to the gas and liquid as it passes than is provided when the mesh is removed and replaced with nothing. More disruption, especially causing the gas/liquid mix to shear as it passes sharp edges in the flow path, leads to a finer foam being formed more quickly.

1% polidocanol solution is used in the first embodiment, but it will be appreciated by those of ordinary skill in this art that there are a number of sclerosing agents which is perform well in the treatment of varicose veins. The most common alternative to polidocanol is sodium tetradecyl sulphate.

In further modifications of the first embodiment, the carbon dioxide gas could be replaced with another appropriate gas which is dissolved in or absorbed by blood or is harmlessly absorbed by the body in some other way. Examples include oxygen, nitrous oxide, helium, neon, xenon. Carbon dioxide, oxygen or a mixture of the two are preferred. Oxygen, although not very soluble, is taken up rapidly by haemoglobin in venous blood and is therefore suitable for use in a foam for injection into varicose veins. Because of its insolubility in water, foams made with oxygen last longer than foams made with carbon dioxide and it is easier to make a fine bubble microfoam with oxygen or another relatively insoluble gas (such as helium or xenon). If oxygen is used instead of carbon dioxide, there is less need for a mesh in the connector device 50.

In a final modification of the first embodiment, a viscosity enhancer may be added to the liquid to increase the lifetime of the foam. This may be particularly useful when a highly soluble gas such as carbon dioxide or a mixture containing a high proportion of carbon dioxide is used. One possible viscosity enhancer is glycerol, which may form between 5 and 50 percent of the volume of the solution, or more preferably between 20 and 40 percent.

The first embodiment, and its various modified versions, may be used in a different method for making foam. It is known to create a foam by attaching a syringe to a vial containing a sclerosing agent and air and then "pumping" the contents of the vial between the syringe and vial by oscillating the plunger of the syringe ("the vial method"). The method is similar in many ways to the so-called "Tessari" method involving two syringes. It will be apparent that the first embodiment and its modified versions described above may all be used in this manner if desired. If this is to be done, the second syringe is dispensed with. The procedure for filling the first syringe is followed as described above, but then the syringe connector 50 is not detached. Instead, the plunger of the syringe is pumped back and forth whilst holding the vial upside down, until an acceptable foam is formed. The syringe is then detached from the connector and the foam used.

The "vial method" as described may also be suitable for automating using a machine similar to the "Turbofoam" machine described above.

Of course, if the vial technique is to be used, much of the structure in the first embodiment becomes redundant, specifically the removable connector 50 and the features on the transfer device 20 designed to engage with it. All that is required is a transfer device having a needle and means for fastening to the vial on one end, and a female luer lock connector on the other end.

It would in theory be possible to carry out this method by simply fitting a syringe with a needle, inserting the needle directly into the vial described above and pumping. A difficulty with this approach is of course that the depth to which the needle penetrates the interior of the vial will determine how much liquid is transferred, and this will be variable unless the user follows a very well defined protocol. For this reason, it is preferred to have a transfer device which is specifically designed to fit the vial such that the needle penetrates the vial to a predetermined extent.

Figure 4:
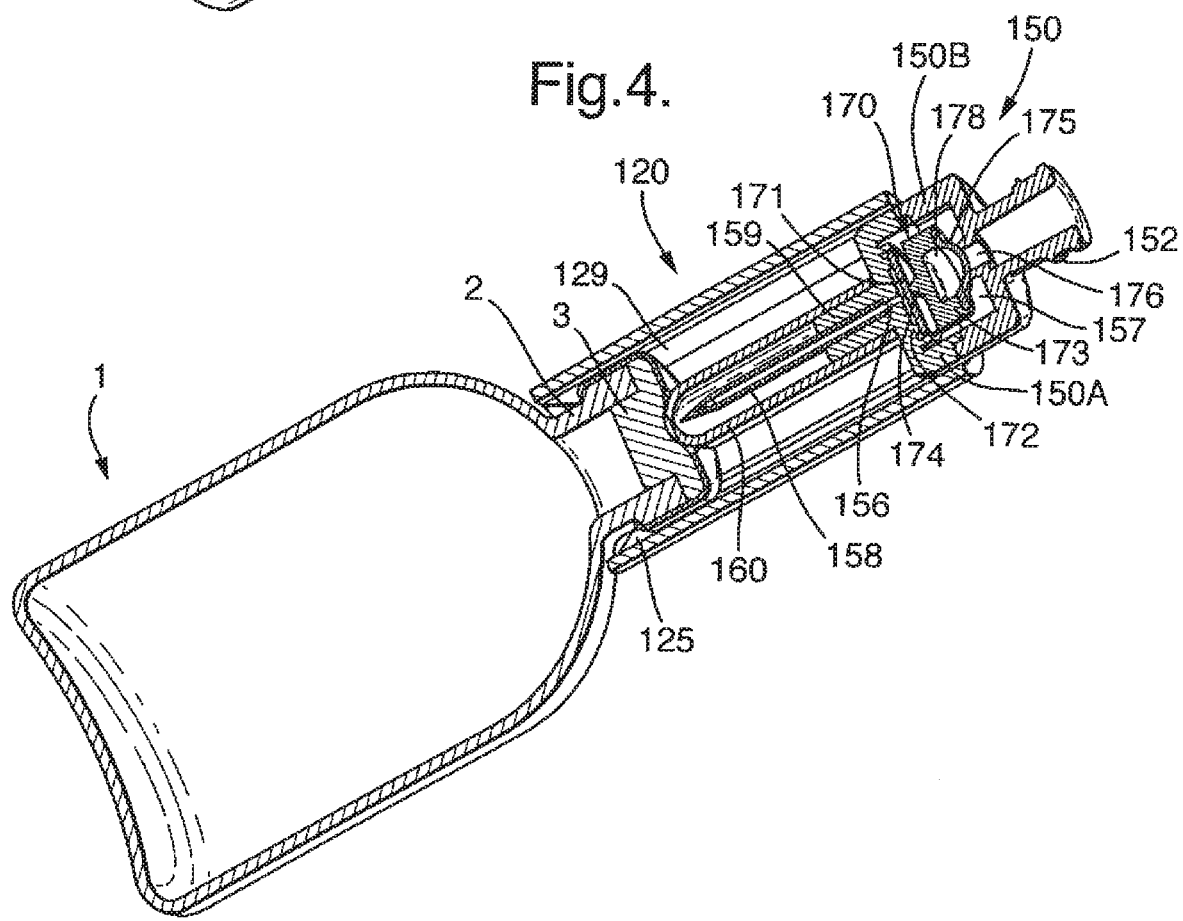
FIG. 4 is a perspective sectional view of a second embodiment of the invention.

A second embodiment in accordance with the invention is illustrated in FIG. 4. Where the parts are the same as in the first embodiment, the same reference numerals will be used to designate those parts.

The second embodiment is designed to be used with a "double piston" type syringe which will be described below. Once such a syringe is charged with gas and liquid, a second plunger in the syringe is oscillated to make foam; all that is required is that the nozzle of the syringe be sealed.

A vial 1 is provided having exactly the same features as that of the first embodiment. A transfer device 120 is shown mounted on the vial. The transfer device is of overall cylindrical shape and is attached to the vial 1 by means of barbed attachment formations 125 which engage the neck region 2 of the vial 1, as for the first embodiment. The reminder of the transfer device, however, is different from the first embodiment and comprises simply a series of axial grooves 129 in the interior wall.

A syringe connector device 150 is received in the transfer device 120. The syringe connector device 150 is formed with axial lands (not shown) complementary to the grooves 129 of the transfer device, which permit axial sliding of the syringe connector device 150 in the transfer device 120. Cooperating formations (not shown) on the syringe connector and transfer devices prevent the syringe connector from being removed from the transfer device 120. In an alternative construction, these formations are frangible in order to permit deliberate removal of the syringe connector, whilst preventing its inadvertent removal.

The syringe connector is made in two halves 150A and 150B, the second half 150B being formed with a female luer lock connector 152 leading to a chamber 157 which in turn communicates with a bore 156 leading to the hollow bore of a needle 158 which is moulded in a boss 159 extending from the first connector half 150A. Inside the chamber 157 is a valve system shown generally at 170 which will be described in detail below. The needle is enclosed in an elastomeric sheath 160 which is mounted in a sealing fashion on the boss 159.

The needle sheath 160 and the valve system 170 both perform the function of sealing a syringe which is attached to the luer connector 152 of the syringe connector device (see description of method below). In the second embodiment, both are provided but in fact either of these means for sealing the syringe could be removed and the device would still work.

The valve system 170 has some similarities to a valve system described in co-pending application number PCT/GB04/003864, the contents of which are incorporated herein by reference. A flat elastomeric disc 171 rests on an annular ridge 172 in the chamber 157. The ridge 172 surrounds the bore 156 so that the elastomeric disc, in its undeformed state, seals the bore 156. Supported centrally in the chamber 157 by means of webs (not shown) is a disc support member 173. Extending from one side of the support member 173 is a relatively small diameter tapered spigot 174 which contacts the surface of the elastomeric disc 171. Mounted on the opposite side of the support member 173 is an elastomeric seal 175 in the shape of a hemisphere with a small flange, the flange being the means by which the seal is attached to the support member 173. The seal 175 has a small slit 177 in its apex, and is in contact with a relatively small diameter annular ridge 176 around the entrance to the luer connector 152, which ridge also encircles the slit 177. The hemispherical seal 175 defines with the support member 173 a cavity 178.

In use, the vial 1, transfer device 120 and syringe connector 150 are supplied pre-assembled. This assembly is supplied together with a double piston syringe (not shown) of a type known in the art, comprising a conventional barrel and plunger together with a further plunger coaxial with the first and operable independently of it. The face of the second plunger is perforated, and in use the second plunger is cycled back and forth within the syringe barrel to agitate the contents and create a foam. Once the foam is created, the first plunger is used to dispense it, as with a normal syringe.

The dual plunger syringe, which is fitted with a luer lock nozzle, is attached to the female luer lock connector making sure that both plungers are depressed fully before attachment. The assembly is then oriented so that the vial is upside down, i.e. with its neck and septum seal pointing downwards, so that the liquid in the vial accumulates adjacent the septum 3. The syringe and the syringe connector 150 are then advanced towards the vial 1, the syringe connector sliding in the transfer device 120 and the needle sheath 160 being pushed back as the needle 158 punctures first the sheath 160 and then the septum 3 of the vial 1. The syringe connector 150 and needle 158 are advanced as far as they will go until either the syringe abuts the end of the transfer device 120 or the boss 159 abuts the septum 3. The penetration depth of the needle into the vial is thus predetermined.

Polidocanol solution (or other sclerosing agent) is then transferred into the syringe via the needle and (if present) the valve system 170, followed by the carbon dioxide (or other gas), as with the first embodiment. The syringe and syringe connector 150 are then retracted so that the needle is no longer inserted into the vial 1. At this point the needle sheath 160 re-seals around the needle. The next phase of the operation may be done with the vial still attached (this is safer in view of the needle 158) or, if the design allows it (see above), the syringe connector is removed, along with the syringe, from the device 120, by breaking frangible components which normally retain the syringe connector 150 in the transfer device 120.

The dual plunger syringe is then manipulated as described above and as is known in the art to produce a suitable foam for sclerotherapy. Whether or not the syringe connector 150 has been removed, the syringe is sealed both by the needle sheath 160 and by the valve system 170. As discussed above, either of these would do the job and therefore they can be seen as alternatives. After the foam has been created, the syringe is disconnected from the female luer 152 on the connector device and the foam is then ready to be dispensed.

The valve system 170 works in the following way. When the needle 158 enters the vial 1, the elastomeric disc 171 is exposed to the relatively high pressure from the vial. The edges of the disc 171 are free to deform away from the annular seat 172 to allow fluid to pass. The chamber 157 is then at "vial pressure". Since the pressure in the chamber 157 is greater than the pressure in the cavity 178 defined by the hemispherical seal 175 and support member 173, the seal 175 will deform. This deformation will allow fluid to pass under the annular ridge 176 and thence to the luer connector 152 and into the syringe.

Once the syringe is filled, the requirement is that the syringe nozzle is sealed whether the pressure is positive or negative on the syringe side of the seal. If the pressure in the syringe is lower, then the seal 175 will be pressed against the annular ridge 176 by the higher pressure in the cavity 178, thereby preventing egress of fluid from the syringe. If the pressure in the syringe is greater, then fluid in the syringe may be able to pass the hemispherical seal as the seal deforms, but the overpressure in the chamber 157 will press the flat disc seal 171 against the annular ridge 172, preventing fluid from passing down the bore 156.

The modifications of the first embodiment concerning the vial contents apply equally to the second embodiment.

Figure 5:
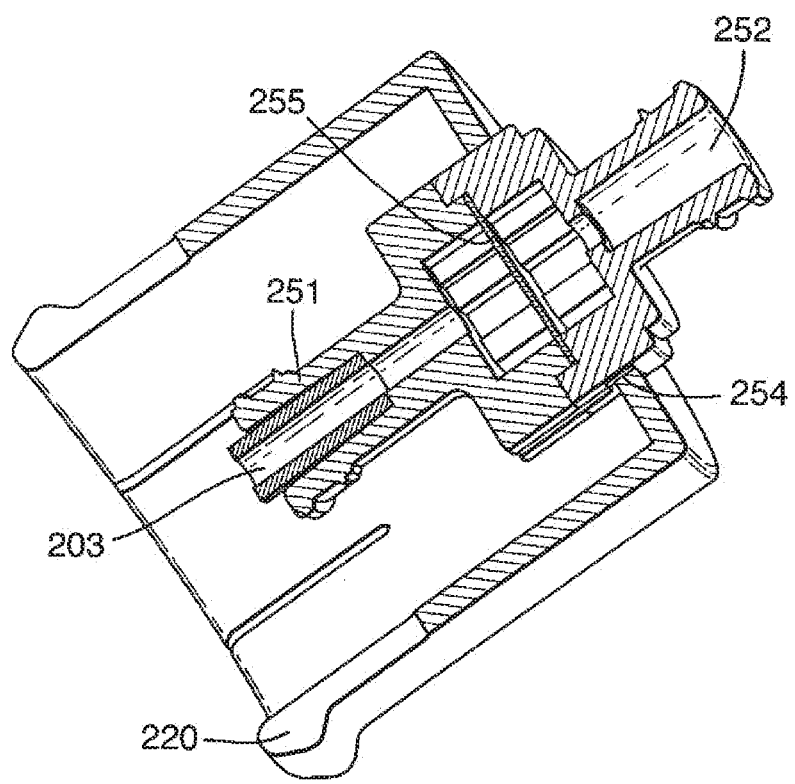
FIG. 5 is a perspective sectional view of a third embodiment of the invention.

A third embodiment of the invention is shown in FIG. 5. This embodiment is in many respects similar to the first. A syringe connector device 250 has all the features of the syringe connector 50 of the first embodiment, except that instead of having locking formations on its outer surface, it is instead connected via a frangible region 254 to a mounting sleeve 220. Thus the connector device is formed in two halves as shown and provided with first and second luer connectors 251, 252 on respective halves of the device. A 5 micron mesh 255 is sandwiched between the two device halves.

The mounting sleeve 220 is a generally cylindrical member with an end plate 221 in which the connector device 250 is mounted by means of the frangible connections 254. The other end of the sleeve 220 is open, and the end of the cylindrical wall is formed with barbed connector formations 225 on the exterior surface. The formations 225 are designed to engage with a metal vial or canister which is provided with a stem valve such as is standard in the field of aerosol canisters. In FIG. 5, the protruding stem of the stem valve is shown at 203. It is formed as a male luer so that it may seal with the female luer 251 of the connector device as shown.

The mounting sleeve and connector assembly are supplied ready-mounted on a canister-type vial (not shown) such that the barbed formations 220, whilst preventing removal of the sleeve 220, allow the assembly to be depressed towards the canister so as to depress the stem 203 and thereby open the canister valve. Once the valve is open, the operation is essentially the same as for the first embodiment. The syringe is filled with the correct volumes of gas and liquid, and then the syringe and connector are twisted to break the frangible connection 254. The syringe and connector are then removed from the sleeve 220 and a second syringe attached to the now exposed female luer 251. Foam is then generated as previously described.

As with the first embodiment, the third embodiment may be modified by replacing the mesh 255 with other structures as described above, and the contents of the canister may also be varied as described above.

In a fourth embodiment, which is not illustrated, the valve system 170 of the second embodiment is incorporated into the connector device of the third embodiment in place of the mesh 255. In this way, the third embodiment may be adapted for use with a double plunger type syringe as described above.

Figure 6:
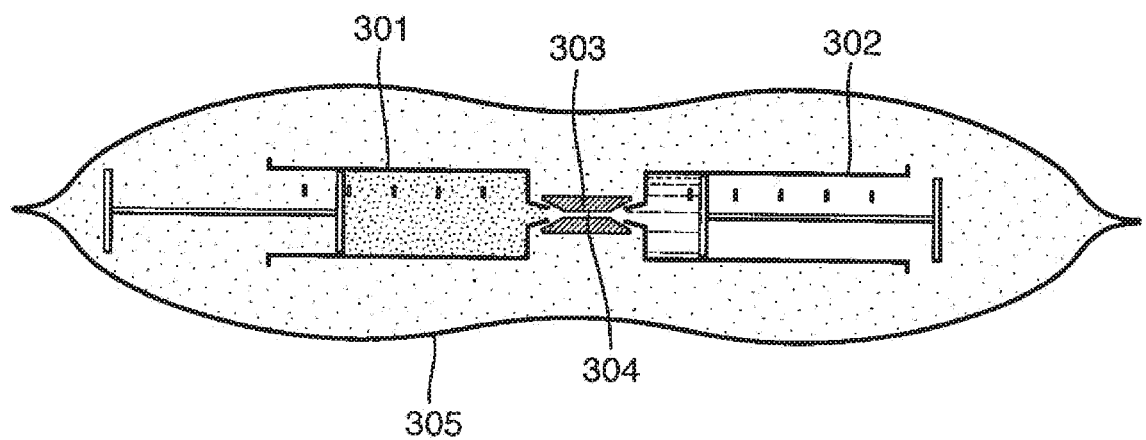
FIG. 6 is a schematic side sectional view of a fifth embodiment of the invention.

A fifth embodiment of the invention is illustrated schematically in FIG. 6. Two 20 ml syringes 301, 302 are supplied, connected together by means of a standard syringe connector 303 having a bore 304 of cross section approximately 1 mm. The first syringe 301 contains 8 ml of substantially pure carbon dioxide whilst the second contains 2 ml of 1% polidocanol solution. The syringes are enclosed in a pouch 305 of metallised plastics laminate, in an atmosphere of substantially pure carbon dioxide at a pressure of 1.1 bar absolute (i.e. 0.1 bar over atmospheric).

To use the fifth embodiment, the user simply breaks open the package and pumps the syringes to produce foam (either manually or using a machine as described above).

In a modified version of the fifth embodiment, the twin syringes are replaced with a double plunger syringe of the type described above, charged with the same quantities of carbon dioxide and 1% polidocanol solution.

The syringes are pre-filled with appropriate volumes of carbon dioxide or other gas as described above, in a sterile hermetic pack. The pack is gas-tight and the syringes are in an atmosphere of carbon dioxide.

What is claimed is:

1. A vessel having sterile contents,
   the contents being predetermined proportions of:
      a first phase comprising a foamable sclerosant liquid solution, and
      a second phase in contact with the first phase comprising a gas mixture consisting essentially of oxygen and carbon dioxide pressurized at a pressure above atmospheric pressure,
   the vessel having a resilient closure, which is pierceable by a hollow hypodermic needle, and which forms a seal around the needle when it is pierced, and
   wherein the vessel is configured for transfer of the sterile contents from the vessel to the syringe through the hypodermic needle inserted through the resilient, pierceable closure and into the foamable sclerosant liquid solution,
   wherein the pressure of the gas mixture in the vessel is selected such that, upon piercing of the resilient closure by the hollow hypodermic needle and passage of the needle into the foamable liquid the pressurized gas mixture forces a volume of the foamable sclerosant liquid solution into the syringe, followed by the passage of a volume of the pressurized gas mixture into the syringe after the needle passes beyond the foamable sclerosant liquid solution in the vessel to thereby form a precursor for a foam; and
   wherein the pressure of the gas mixture in the vessel is selected such that pressures in the vessel and syringe equalize once a predetermined volume of the foamable sclerosant liquid solution and a predetermined volume of the pressurized gas mixture have been transferred to the syringe.

2. The vessel as claimed in claim 1, wherein the closure is a rubber septum.

3. The vessel as claimed in claim 2, wherein the rubber septum has a thickness of between 2 and 10 mm.

4. The vessel as claimed in claim 2, wherein the rubber septum comprises a chlorobutyl or bromobutyl rubber material.

5. The vessel as claimed in claim 1, wherein the contents of the vessel are at a pressure of 1.3 bara or more and less than 10 bara.

6. The vessel as claimed in claim 1, wherein the foamable sclerosant liquid solution is a solution of polidocanol.

7. The vessel as claimed in claim 1, wherein the foamable sclerosant liquid solution is a 1% (vol/vol) solution of polidocanol.

8. The vessel as claimed in claim 1, wherein the ratio of liquid solution to gas mixture is in the range of 0.05 g/ml to 0.25 g/ml.

9. The vessel as claimed in claim 1, wherein the ratio of liquid solution to gas mixture is in the range of 0.07 g/ml to 0.2 g/ml.

10. The vessel as claimed in claim 1, wherein the ratio of liquid solution to gas mixture is in the range of 0.1 g/ml to 0.16 g/ml.

\* \* \* \* \*